US009265713B2

(12) United States Patent
Ramadan et al.

(10) Patent No.: US 9,265,713 B2
(45) Date of Patent: Feb. 23, 2016

(54) COSMETIC COMPOSITIONS HAVING LONG LASTING SHINE

(71) Applicant: L'OREAL, Paris (FR)

(72) Inventors: Fatima Ramadan, Marlboro, NJ (US); Hy Si Bui, Piscataway, NJ (US)

(73) Assignee: L'OREAL S.A. (FR)

( * ) Notice: Subject to any disclaimer, the term of this patent is extended or adjusted under 35 U.S.C. 154(b) by 0 days.

(21) Appl. No.: 14/162,243

(22) Filed: Jan. 23, 2014

(65) Prior Publication Data

US 2014/0140945 A1 May 22, 2014

Related U.S. Application Data

(63) Continuation of application No. 13/035,441, filed on Feb. 25, 2011, now abandoned.

(51) Int. Cl.
| | |
|---|---|
| *A61K 8/81* | (2006.01) |
| *A61K 8/92* | (2006.01) |
| *A61K 8/85* | (2006.01) |
| *A61K 8/90* | (2006.01) |
| *A61K 8/37* | (2006.01) |
| *A61K 8/60* | (2006.01) |
| *A61Q 1/06* | (2006.01) |

(52) U.S. Cl.
CPC ............. *A61K 8/8194* (2013.01); *A61K 8/375* (2013.01); *A61K 8/60* (2013.01); *A61K 8/8117* (2013.01); *A61K 8/85* (2013.01); *A61K 8/90* (2013.01); *A61K 8/92* (2013.01); *A61K 8/927* (2013.01); *A61Q 1/06* (2013.01); *A61K 2800/594* (2013.01)

(58) Field of Classification Search
CPC ....... A61K 8/8194; A61K 8/92; A61K 8/927; A61K 8/60; A61K 2800/594; A61Q 1/06
See application file for complete search history.

(56) References Cited

U.S. PATENT DOCUMENTS

| | | |
|---|---|---|
| 2,823,195 A | 2/1958 | Shorr et al. |
| 2,823,218 A | 2/1958 | Speier et al. |
| 3,723,566 A | 3/1973 | Thompson et al. |
| 4,116,924 A | 9/1978 | Peabody |
| 4,164,563 A | 8/1979 | Chang |
| 4,322,400 A | 3/1982 | Yuhas |
| 4,369,284 A | 1/1983 | Chen |
| 4,492,428 A | 1/1985 | Levy |
| 4,529,605 A | 7/1985 | Lynch et al. |
| 4,656,213 A | 4/1987 | Schlademan |
| 4,693,935 A | 9/1987 | Mazurek |
| 4,725,658 A | 2/1988 | Thayer et al. |
| 4,822,852 A | 4/1989 | Wittmann et al. |
| 4,913,235 A | 4/1990 | Harris et al. |
| 4,972,037 A | 11/1990 | Garbe et al. |
| 4,976,961 A | 12/1990 | Norbury et al. |
| 4,981,902 A | 1/1991 | Mitra et al. |
| 4,981,903 A | 1/1991 | Garbe et al. |
| 5,061,481 A | 10/1991 | Suzuki et al. |
| 5,209,924 A | 5/1993 | Garbe et al. |
| 5,219,560 A | 6/1993 | Suzuki et al. |
| 5,221,534 A | 6/1993 | DesLauriers et al. |
| 5,246,694 A | 9/1993 | Birtwistle |
| 5,262,087 A | 11/1993 | Tachibana et al. |
| 5,262,505 A | 11/1993 | Nakashima et al. |
| 5,272,241 A | 12/1993 | Lucarelli et al. |
| 5,294,438 A | 3/1994 | Chang et al. |
| 5,334,737 A | 8/1994 | Thimineur et al. |
| 5,407,986 A | 4/1995 | Furukawa et al. |
| 5,412,004 A | 5/1995 | Tachibana et al. |
| 5,468,477 A | 11/1995 | Kumar et al. |
| 5,473,041 A | 12/1995 | Itoh |
| 5,492,945 A | 2/1996 | Morita et al. |
| 5,538,793 A | 7/1996 | Inokuchi et al. |
| 5,567,428 A | 10/1996 | Hughes |
| 5,618,883 A | 4/1997 | Plamthottam et al. |
| 5,648,066 A | 7/1997 | Stepniewski |
| 5,653,968 A | 8/1997 | Carballada et al. |
| 5,656,286 A | 8/1997 | Miranda et al. |
| 5,690,918 A | 11/1997 | Jacks et al. |
| 5,725,882 A | 3/1998 | Kumar et al. |
| 5,726,220 A | 3/1998 | Tokushige et al. |
| 5,756,082 A | 5/1998 | Cashin et al. |
| 5,756,568 A | 5/1998 | Morita et al. |
| 5,837,223 A | 11/1998 | Barone et al. |
| 5,843,407 A | 12/1998 | El-Nokaly et al. |

(Continued)

FOREIGN PATENT DOCUMENTS

| | | |
|---|---|---|
| CA | 2278685 A1 | 8/1998 |
| CN | 1246787 A | 3/2000 |

(Continued)

OTHER PUBLICATIONS

"Koboguard ® 5400 Oil soluble film former", Technical Literature ref KG54-001, Jan. 8, 2010.
C. M. Hansen: "The three-dimensional solubility parameters" J. Paint Technol., 39, 105 (1967), pp. 104-117.
Eric A. Grulke, "Solubility Parameter Values", Polymer Handbook 3rd edition, edited by J. Brandrup and E. H. Immergut, Chapter VII, 1989, pp. 519-559, A Wiley-Interscience Publication, John Wiley & Sons.
J. Wenninger and G.N. McEwen, Jr., International Cosmetic Ingredient Dictionary, 1995, 6th edition, vol. 1 & 2, Published by The Cosmetic, Toiletry, and Fragrance Association, Washington, DC.
Chinese Communication dated Mar. 5, 2010 as received in corresponding Chinese application No. 200710128891.9.

(Continued)

*Primary Examiner* — Bethany Barham
*Assistant Examiner* — Barbara Frazier
(74) *Attorney, Agent, or Firm* — Lerner, David, Littenberg, Krumholz & Mentlik, LLP

(57) ABSTRACT

The present invention is directed to a cosmetic composition containing: a) a block copolymer; b) a primary tackifier; c) a high viscosity ester; d) an alkoxylated mixed polyester; e) a wax; f) a solvent; and g) optionally, a colorant. The invention is also directed to a method of making up keratinous substrates involving applying onto the keratinous substrates said composition.

40 Claims, No Drawings

(56) References Cited

U.S. PATENT DOCUMENTS

| | | |
|---|---|---|
| 5,874,069 A | 2/1999 | Mendolia et al. |
| 5,919,441 A | 7/1999 | Mendolia et al. |
| 5,945,471 A | 8/1999 | Morita et al. |
| 5,948,393 A | 9/1999 | Tomomasa et al. |
| 5,959,009 A | 9/1999 | Konik et al. |
| 5,969,172 A | 10/1999 | Nye |
| 5,981,680 A | 11/1999 | Petroff et al. |
| 5,985,297 A | 11/1999 | Mellul et al. |
| 6,024,822 A | 2/2000 | Alper et al. |
| 6,045,782 A | 4/2000 | Krog et al. |
| 6,051,216 A | 4/2000 | Barr et al. |
| 6,060,072 A | 5/2000 | Konik et al. |
| 6,083,516 A | 7/2000 | Curtis et al. |
| 6,103,250 A | 8/2000 | Brieva et al. |
| 6,114,424 A | 9/2000 | Lahanas et al. |
| 6,177,091 B1 | 1/2001 | Bara et al. |
| 6,200,581 B1 | 3/2001 | Lin et al. |
| 6,248,339 B1 | 6/2001 | Knitowski et al. |
| 6,258,347 B1 | 7/2001 | Sakuta et al. |
| 6,267,951 B1 | 7/2001 | Shah et al. |
| 6,309,629 B1 | 10/2001 | Travkina et al. |
| 6,338,839 B1 | 1/2002 | Auguste et al. |
| 6,340,467 B1 | 1/2002 | Morrison |
| 6,348,152 B1 | 2/2002 | Kawahara et al. |
| 6,353,076 B1 | 3/2002 | Barr et al. |
| 6,362,287 B1 | 3/2002 | Chorvath et al. |
| 6,362,288 B1 | 3/2002 | Brewer et al. |
| 6,376,078 B1 | 4/2002 | Inokuchi |
| 6,387,358 B2 | 5/2002 | Chuah et al. |
| 6,403,070 B1 | 6/2002 | Pataut et al. |
| 6,423,324 B1 | 7/2002 | Murphy et al. |
| 6,426,062 B1 | 7/2002 | Chopra et al. |
| 6,433,163 B1 | 8/2002 | Ho |
| 6,451,295 B1 | 9/2002 | Cai et al. |
| 6,503,491 B2 | 1/2003 | Guenin et al. |
| 6,503,632 B1 | 1/2003 | Hayashi et al. |
| 6,517,818 B1 | 2/2003 | Golz-Berner et al. |
| 6,524,598 B2 | 2/2003 | Sunkel et al. |
| 6,541,017 B1 | 4/2003 | Lemann et al. |
| 6,544,642 B2 | 4/2003 | Cinelli et al. |
| 6,566,026 B2 | 5/2003 | Watanabe et al. |
| 6,569,955 B1 | 5/2003 | Brewer et al. |
| 6,656,458 B1 | 12/2003 | Philippe et al. |
| 6,682,748 B1 | 1/2004 | De La Poterie et al. |
| 6,811,770 B2 | 11/2004 | Ferrari et al. |
| 6,916,464 B2 | 7/2005 | Hansenne et al. |
| 6,958,155 B2 | 10/2005 | Lu et al. |
| 6,960,339 B1 | 11/2005 | Ferrari |
| 7,078,026 B2 | 7/2006 | Ferrari et al. |
| 7,083,800 B1 | 8/2006 | Terren et al. |
| 7,321,011 B2 | 1/2008 | Lu et al. |
| 7,329,699 B2 | 2/2008 | Liew et al. |
| 7,884,158 B2 | 2/2011 | Bui et al. |
| 7,887,786 B2 | 2/2011 | Tournilhac et al. |
| 7,993,661 B2 | 8/2011 | Arnaud et al. |
| 2002/0028223 A1 | 3/2002 | Vatter et al. |
| 2002/0031488 A1 | 3/2002 | Kanji et al. |
| 2002/0031968 A1 | 3/2002 | Hamaguchi et al. |
| 2002/0048557 A1 | 4/2002 | Cai et al. |
| 2002/0051758 A1 | 5/2002 | Cai et al. |
| 2002/0114773 A1 | 8/2002 | Kanji et al. |
| 2003/0035944 A1 | 2/2003 | Blackwell |
| 2003/0039620 A1 | 2/2003 | Rodriguez et al. |
| 2003/0059448 A9 | 3/2003 | Kanji et al. |
| 2003/0068344 A1 | 4/2003 | Ferrari et al. |
| 2003/0068348 A1 | 4/2003 | Ferrari et al. |
| 2003/0072730 A1 | 4/2003 | Tournilhac |
| 2003/0082129 A1 | 5/2003 | Buckingham et al. |
| 2003/0170188 A1 | 9/2003 | Ferrari et al. |
| 2003/0228333 A1 | 12/2003 | Fecht et al. |
| 2003/0232030 A1 | 12/2003 | Lu et al. |
| 2003/0235548 A1 | 12/2003 | Lu |
| 2003/0235552 A1 | 12/2003 | Yu |
| 2003/0235553 A1 | 12/2003 | Lu et al. |
| 2004/0001799 A1 | 1/2004 | Lu et al. |
| 2004/0009198 A1 | 1/2004 | Bernard et al. |
| 2004/0047884 A1 | 3/2004 | Bernard et al. |
| 2004/0052745 A1 | 3/2004 | Bernard et al. |
| 2004/0076594 A1 | 4/2004 | Legrand |
| 2004/0115153 A1 | 6/2004 | Yu |
| 2004/0115154 A1 | 6/2004 | Yu |
| 2004/0120912 A1 | 6/2004 | Yu |
| 2004/0126336 A1 | 7/2004 | Hansenne et al. |
| 2004/0137028 A1 | 7/2004 | de la Poterie |
| 2004/0180032 A1 | 9/2004 | Manelski et al. |
| 2004/0197285 A1 | 10/2004 | Van Dort |
| 2004/0223936 A1 | 11/2004 | Fecht et al. |
| 2004/0223989 A1 | 11/2004 | Auguste et al. |
| 2004/0234612 A1 | 11/2004 | Blin et al. |
| 2004/0258642 A1 | 12/2004 | Calello et al. |
| 2005/0009989 A1 | 1/2005 | Liew et al. |
| 2005/0020769 A1 | 1/2005 | Lu et al. |
| 2005/0061435 A1 | 3/2005 | Everaerts et al. |
| 2005/0069564 A1 | 3/2005 | Eversheim et al. |
| 2005/0089492 A1 | 4/2005 | Lu et al. |
| 2005/0158260 A1 | 7/2005 | Ferrari et al. |
| 2005/0228115 A1 | 10/2005 | Auguste et al. |
| 2005/0245673 A1 | 11/2005 | Ferrari et al. |
| 2005/0287105 A1 | 12/2005 | Blin et al. |
| 2006/0013839 A1 | 1/2006 | Yu |
| 2006/0029560 A1 | 2/2006 | Blin |
| 2006/0030685 A1 | 2/2006 | Passade Boupat et al. |
| 2006/0099168 A1 | 5/2006 | Corzani et al. |
| 2006/0110345 A1 | 5/2006 | Lu et al. |
| 2006/0120983 A1 | 6/2006 | Blin et al. |
| 2006/0165626 A1 | 7/2006 | Ricard et al. |
| 2006/0171910 A1 | 8/2006 | Ricard et al. |
| 2006/0193801 A1 | 8/2006 | Blin et al. |
| 2006/0204470 A1 | 9/2006 | Tournilhac |
| 2007/0020205 A1 | 1/2007 | Blin et al. |
| 2007/0041920 A1 | 2/2007 | Blin et al. |
| 2007/0041928 A1 | 2/2007 | Chen et al. |
| 2007/0053859 A1 | 3/2007 | Bui et al. |
| 2007/0055014 A1 | 3/2007 | Lu et al. |
| 2007/0142521 A1 | 6/2007 | Brahms et al. |
| 2007/0149703 A1 | 6/2007 | Caprasse et al. |
| 2007/0212317 A1 | 9/2007 | Atis et al. |
| 2007/0258923 A1 | 11/2007 | Bui et al. |
| 2007/0258924 A1 | 11/2007 | Bui et al. |
| 2007/0258925 A1 | 11/2007 | Bui et al. |
| 2007/0258932 A1 | 11/2007 | Bui et al. |
| 2007/0258933 A1 | 11/2007 | Bui et al. |
| 2007/0258934 A1 | 11/2007 | Bui et al. |
| 2008/0102049 A1 | 5/2008 | McDermott |
| 2008/0171006 A1 | 7/2008 | Bui et al. |
| 2008/0171007 A1 | 7/2008 | Bui |
| 2008/0171008 A1 | 7/2008 | Bui |
| 2008/0254076 A1 | 10/2008 | Ferrari et al. |
| 2010/0098648 A1 | 4/2010 | Yu |
| 2012/0219516 A1 | 8/2012 | Ramada et al. |

FOREIGN PATENT DOCUMENTS

| | | |
|---|---|---|
| CN | 1646656 A | 7/2005 |
| CN | 1761446 A | 4/2006 |
| EP | 0377447 A2 | 7/1990 |
| EP | 0594285 A2 | 4/1994 |
| EP | 0693517 A1 | 1/1996 |
| EP | 0600445 A3 | 3/1996 |
| EP | 0850649 A1 | 7/1998 |
| EP | 0923928 A1 | 6/1999 |
| EP | 1048686 A2 | 11/2000 |
| EP | 0682940 B1 | 1/2001 |
| EP | 1068856 A1 | 1/2001 |
| EP | 0975320 B1 | 12/2001 |
| EP | 1266647 A1 | 12/2002 |
| EP | 1266648 A1 | 12/2002 |
| EP | 0966263 B1 | 3/2005 |
| EP | 1582203 A1 | 10/2005 |
| EP | 1005322 B1 | 11/2005 |
| EP | 1946745 A2 | 7/2008 |
| FR | 2765800 A1 | 1/1999 |
| FR | 2785530 A1 | 5/2000 |
| FR | 2842100 A1 | 1/2004 |

(56) References Cited

FOREIGN PATENT DOCUMENTS

| | | | |
|---|---|---|---|
| FR | 2873030 A1 | 1/2006 |
| GB | 1348783 A | 3/1974 |
| JP | 60255713 A | 12/1985 |
| JP | 06-024969 | 2/1994 |
| JP | 2602053 B2 | 4/1997 |
| JP | 2657219 B2 | 9/1997 |
| JP | 2000178126 A | 6/2000 |
| JP | 2001097852 A | 4/2001 |
| JP | 2001507591 A | 6/2001 |
| JP | 2001511161 A | 8/2001 |
| JP | 2002097366 A | 4/2002 |
| JP | 2002154916 A | 5/2002 |
| JP | 2002528477 A | 9/2002 |
| JP | 2003516949 A | 5/2003 |
| JP | 2004035567 A | 2/2004 |
| JP | 2004051850 A | 2/2004 |
| JP | 2004115774 A | 4/2004 |
| JP | 2004256539 A | 9/2004 |
| JP | 2005225867 A | 8/2005 |
| JP | 2005247730 A | 9/2005 |
| JP | 2005528471 A | 9/2005 |
| JP | 2006028181 A | 2/2006 |
| JP | 2007297391 A | 11/2007 |
| JP | 2007532754 A | 11/2007 |
| JP | 2008512498 A | 4/2008 |
| JP | 2009521549 A | 6/2009 |
| KR | 9002521 | 4/1990 |
| WO | 9736572 | 10/1997 |
| WO | 9736573 A1 | 10/1997 |
| WO | 9824588 A1 | 6/1998 |
| WO | 9906473 A1 | 2/1999 |
| WO | 9947111 A1 | 9/1999 |
| WO | 0109239 A1 | 2/2001 |
| WO | 0197758 A2 | 12/2001 |
| WO | 0217870 A2 | 3/2002 |
| WO | 0217871 A2 | 3/2002 |
| WO | 02089760 A1 | 11/2002 |
| WO | 03013447 A2 | 2/2003 |
| WO | 03/042221 A1 | 5/2003 |
| WO | 03087254 A2 | 10/2003 |
| WO | 03101412 A2 | 12/2003 |
| WO | 03105788 A2 | 12/2003 |
| WO | 2004054523 A1 | 7/2004 |
| WO | 2004054524 A1 | 7/2004 |
| WO | 2004066918 A2 | 8/2004 |
| WO | 2005100444 A1 | 10/2005 |
| WO | 2007008575 A1 | 1/2007 |
| WO | 2007031872 A2 | 3/2007 |
| WO | 2007015166 A3 | 4/2007 |
| WO | 2007078825 A2 | 7/2007 |

OTHER PUBLICATIONS

Chinese Communication dated May 15, 2009 as received in corresponding Chinese application No. 200710128891.9.
Chinese Communication dated May 8, 2009 as received in corresponding Chinese application No. 200710128890.4.
Chinese Communication dated May 9, 2011 as received in corresponding Chinese application No. 200710128890.4.
Chinese Communication dated Nov. 17, 2010 as received in corresponding Chinese application No. 200710128891.9.
Co-pending U.S. Appl. No. 10/166,755, US Title: Cosmetic composition for care and/or makeup, structured with silicone polymers and film-forming silicone resins U.S. Filing Date: Jun. 12, 2002.
Co-pending U.S. Appl. No. 10/166,760, US Title: Compositions containing at least one oil structured with at least one silicone-polyamide polymer, and at least one film-forming polymer and methods thereof. U.S. Filing Date: Jun. 12, 2002.
Co-pending U.S. Appl. No. 11/485,283 US-Title: Two-coat cosmetic product, uses thereof and makeup kit containing this product Filing Date: Jul. 13, 2006.
Co-pending U.S. Appl. No. 11/485,347 Title: Lip makeup composition with good staying power comprising a low molecular weight resin US Filing Date: Jul. 13, 2006.
Co-pending U.S. Appl. No. PCT/US06/26310 Title: Cosmetic Compositions Containing Liposoluble Polymers and Tackifiers-PCT Filing Date: Jul. 7, 2006.
Co-pending U.S. Appl. No. 11/219,946 Title: Cosmetic compositions containing block copoymers, tackifiers and phenylated silicones—US Filing Date: Sep. 6, 2005.
Co-pending U.S. Appl. No. 11/417,975 Title: Cosmetic compositions containing block copolymers. tackifiers and a solvent mixture—US Filing Date: May 3, 2006.
Co-pending U.S. Appl. No. 11/417,977 Title: Cosmetic compositions containing block copolymers, tackifiers and shine enhancing agents—us Filing Date: May 3, 2006.
Co-pending U.S. Appl. No. 11/417,981 Title: Cosmetic compositions containing block copolymers, tackifiers and modified silicones—US Filing Date: May 3, 2006.
Co-pending U.S. Appl. No. 11/417,986 Title: Cosmetic compositions containing block copolymers, tackifiers and a selective solvent for hard blocks—US Filing Date: May 3, 2006.
Co-pending U.S. Appl. No. 11/418,327 Title: Cosmetic compositions containing block copolymers, tackifiers and gelling agents—US Filing Date: May 3, 2006.
DC 2-8179. http://www.dowcorning.com/applications/search/default.aspx?R=1436EN. Accessed Jan. 5, 2009.
Dow Corning 2-8178 Gellant, Ref. No. 27-1055B-01, Apr. 16, 2003, 6 pp.
Dow Corning® 2-8178 Gellant, Product Information Personal Care, 6 pp., Aug. 13, 2002.
Dow Corning® 2-8178 Gellant, Ref. No. 27-1055-01, Aug. 2002, 35 pp.
European Communication dated Apr. 24, 2008 as received in corresponding European application No. 07008772.1.
European Communication dated Mar. 16, 2010 as received in corresponding European Application No. 07008772.1.
European Communication dated Mar. 31, 2008 as received in corresponding European application No. 07008771.3.
European Search Report as received in corresponding European application No. 07008772.1, Feb. 18, 2008.
European Search Report as received in corresponding European application No. 07008771.3 dated Jan. 17, 2008.
Factsheet—Dow Corning 670 Fluid—Intellectual Property Statement—Apr. 14, 2005.
Hansen, Paint and Coating Testing Manual, 1995, Joseph V. Koleske Editor., pp. 383-404.
International Search Report and Written Opinion for Application No. PCT/EP2012/052719 dated Dec. 12, 2013.
Japanese Communication dated Mar. 1, 2011 as received in corresponding Japanese application No. 2007-121913.
Japanese Communication dated Mar. 1, 2011 as received in corresponding Japanese Application No. 2007-121914.
Japanese Communication dated Nov. 17, 2009 as received in corresponding Japanese Application No. 2007-121914.
JET magazine. Lip service: how to create luscious lips that last. Sep. 9, 2002. Johnson Publishing Company. vol. 102, No. 12. p. 22. Also available electronically at http://books.google.com/books?id=lbYDAAAAMBAJ&pg=PA22dq=lip+gloss+and+lipstick+application+together#v=onepage&q=&f=false.
McCutcheon's, Detergents and Emulsifiers, North American Edition {2003), Allured Publishing Corporation.
Shin-Etsu Silicones for Personal Care; Product Brochure, KSP-200-300, "Hybrid Silicone Powders containing Fluoroalkyl or Phenyl group for Personal Care", 2001.
Shin-Etsu Silicones for Personal Care; Product Brochure, KSP-100•101•102•103•104•105 "Hybrid Silicone Powders for Personal Care" 2000.
Silkflo Technical Sheet, http://www.in-cosmeticsasia.com/Exhibitorlibrary/205/Sellsheet_-Silkflo_new_Aug07 2.pdf, obtained online on Sep. 2, 2009.
U.S. Appl. No. 11/972,102 dated Jan. 10, 2008.
U.S. Appl. No. 11/972,143 dated Jan. 10, 2008.
U.S. Appl. No. 11/972,161 dated Jan. 10, 2008.
U.S. Appl. No. 11/972,839 dated Jan. 11, 2008.

(56) References Cited

OTHER PUBLICATIONS

Virginie Caprasse, Isabelle Van Reeth, Dow Corning S.A., Research Disclosure, A new silicone resin for personal care applications, Research Disclosure Database No. 486008, Published in Oct. 2004 (Eiectronic publication date: Sep. 10, 2004 ), Research Disclosure Journal, Kenneth Mason Publications Ud., The Book Barn, Westbourne, Hants. P010 8RS UK.

Zhang et al., J. Colloid Interface Science, 2003, 266, 339-345.

COSMETIC COMPOSITIONS HAVING LONG LASTING SHINE

CROSS-REFERENCE TO RELATED APPLICATION

The present application is a continuation of U.S. patent application Ser. No. 13/035,441, filed on Feb. 25, 2011, the disclosure of which is incorporated herein by reference.

BACKGROUND OF THE INVENTION

Cosmetic compositions used to make up or enhance the appearance of keratinous substrates such as skin, lips, hair and eyelashes are oftentimes required to be able to impart various properties such as high shine or gloss, long lasting shine and good or long wear of color. However, the formulation of cosmetic products that can deliver all these properties at the same time can pose some challenges. For example, cosmetic compositions using traditional ingredients known to impart shine or gloss, such as oils, have very poor wear properties. In order to overcome these problems, film forming resins such as silicone film forming resins are generally employed to improve the wear of cosmetic compositions. While the use of silicone film forming resins in cosmetics is popular, one drawback associated with their use is that they tend to be brittle and flake off.

Alternatively, two step products have been developed, using a topcoat to provide shine and/or comfort to a basecoat which is matte and/or dry in an effort to provide good wear and long-lasting shine at the same time. However, this presents the drawback of having to formulate two different compositions and to the consumer who has to employ two separate products.

Thus, it is an object of the present invention to provide a method and composition for making-up a keratinous substrate such as skin or hair in a manner which delivers a combination of good wear, liquid-like shine effect and long lasting shine properties, as well as a non-tacky feel, comfort, cushion, moisturization and desirable creamy texture characteristics upon application onto skin. At the same time, it is also an object of the present invention to provide cosmetic compositions, particularly, lipstick compositions, that have minimum feathering and migration properties.

BRIEF SUMMARY OF THE INVENTION

A first aspect of the present invention is directed to a method of making up keratinous substrates involving applying onto the keratinous substrates a composition containing: a) at least one block copolymer; b) at least one primary tackifier; c) at least one high viscosity ester; d) at least one alkoxylated mixed polyester; e) at least one wax; f) at least one solvent; and g) optionally, a colorant.

A second aspect of the present invention is directed to a cosmetic composition comprising: a) at least one block copolymer; b) at least one primary tackifier; c) at least one high viscosity ester; d) at least one alkoxylated mixed polyester; e) at least one wax; f) at least one solvent; and g) optionally, a colorant.

It has been surprisingly discovered that the use of the above-disclosed cosmetic composition delivers long wear of color, a liquid-like shine effect, and long lasting shine, while exhibiting minimal feathering and migration disadvantages.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" or "film-forming polymer" as used herein means a polymer or resin that leaves a film on the substrate to which it is applied, for example, after a solvent accompanying the film former has evaporated, absorbed into and/or dissipated on the substrate.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to lips and evaluating the color of the composition after an extended period of time. For example, the color of a composition may be evaluated immediately following application to lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is 50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The cosmetic compositions and methods of the present invention can comprise, consist of, or consist essentially of the essential elements and limitations of the invention described herein, as well as any additional or optional ingredients, components, or limitations described herein or otherwise useful in personal care.

Block Copolymer

The block copolymers of the present invention are characterized by the presence of at least one "hard" segment, and at least one "soft" segment. Aside from their compositional nature, the hard and soft segments of the block copolymers of the present invention are defined in terms of their respective glass transition temperatures, "$T_g$". More particularly, the hard segment has a $T_g$ of 50° C. or more, whereas the soft segment has a $T_g$ of 20° C. or less. The glass transition temperature $T_g$ for the hard block can range from 50° C. to 150° C.; 60° C. to 125° C.; 70° C. to 120° C.; 80° C. to 110° C. The glass transition temperature $T_g$ for the soft segment of the block copolymer can range from 20° C. to −150° C.; 0° C. to −135° C.; −10° C. to −125° C.; −25° C. to −100° C. A more in depth explanation can be found in U.S. Pat. Nos. 5,294,438 and 6,403,070, the entire contents of which are hereby incorporated by reference.

One type of block copolymer which may be employed by the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In some embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

The amounts of the block (co)polymer or (co)polymers, as well as their structure (di-block, tri-block, etc.), affect the nature of the thermoplastic elastomer, including its gelled form, which may range from fragile to soft/flexible to firm. For instance, soft gels contain relatively high amounts of soft segments, and firm gels contain relatively high amounts of hard segments. The overall properties of the composition may also be affected by including more than one such block copolymer e.g., including a mixture of copolymers. For example, the presence of tri-block copolymers enhances the integrity of the film formed. The gel may also be transparent, translucent or opaque, depending upon the other cosmetically acceptable ingredients added, as described herein.

It is preferred that the styrene content of the block copolymer be less than 30% by weight, preferably less than 25% by weight, and more preferably less than 20% by weight, based on the weight of the block copolymer. This is because of the tendency of block copolymers having a styrene content of greater than 30% by weight to harden/gel in conventional carrier systems. However, in the event that a block copolymer having a styrene content of greater than 30% by weight is used, it may be necessary to also employ a co-solvent or functional ingredient capable of dissolving a styrene block in an amount effective to control the hardening/gelling of the styrene-containing elastomer in the cosmetic composition.

Particularly preferred block copolymers include di-block copolymers comprised of a styrene monomer in combination with at least one second monomer chosen from ethylene and butylene; tri-block copolymers comprised of at least two styrene monomers in combination with at least one second monomer chosen ethylene and butylene; and mixtures of di-block and tri-block copolymers.

A particularly preferred block copolymer for use in the present invention is a mixture of at least one di-block copolymer and at least one tri-block copolymer wherein the di- and tri-block copolymers are comprised of at least one styrene monomer in combination with at least one additional monomer chosen from ethylene and butylene. A particularly preferred block copolymer is Kraton G16571\4® (also known as hydrogenated styrene/butadiene copolymer) which is comprised of 29% by weight of a di-block copolymer and 71% by weight of a tri-block copolymer, all weights based on the total weight of the block copolymer, commercially available from Kraton Polymers. It should be noted, however, that any thermoplastic elastomer of the block copolymer type having at least one soft and at least one hard segment may be used without departing from the spirit of the invention.

The at least one block copolymer is present in the composition of the invention in an amount ranging from about 0.1 to about 30% by weight, preferably from about 1% to about 20% by weight, or more preferably from about 5% to about 10% by weight, relative to the total weight of the composition.

Primary Tackifier

A substance is described as a tackifier if, by adding it to a block copolymer, the resulting composition has the properties of a pressure sensitive adhesive. In general, tackifiers can be divided into four different families in terms of their chemistry: hydrocarbon resins, terpenes, amorphous (i.e. non-crystalline) rosins, rosin esters and their derivatives, and pure monomer resins. These tackifiers are characterized by their compatibility with at least one segment of the block copolymer. By the term "compatible", it is meant that when the block copolymer and tackifier are mixed, the combination of at least one segment of the block copolymer with the tackifier forms a polymer blend having a single glass transition temperature $T_g$ which may be measured by DMA, DSC or neutron light scattering.

The compatibility of the block copolymer and the tackifier may also be defined in terms of solubility parameters. The solubility parameter δ according to the Hansen solubility space is defined in the article "*Solubility Parameter Values*" by Eric A. Grulke in the work "*Polymer Handbook*" 3rd edition, Chapter VII, pages 519-559, the entire content of which is hereby incorporated by reference, by the relationship:

$$\delta=(d_D^2+d_P^2+d_H^2)^{1/2},$$

in which:
  $d_D$ characterizes the London dispersion forces resulting from the formation of dipoles induced during molecular impacts,
  $d_P$ characterizes the forces of Debye interactions between permanent dipoles,
  $d_H$ characterizes the forces of specific interactions (hydrogen bond, acid/base or donor/acceptor type and the like). The definition of the solvents in the three-dimensional solubility space according to Hansen is given in the article by C. M. Hansen: "*The three-dimensional solubility parameters*" J. Paint Technol., 39, 105(1967), the entire content of which is hereby incorporated by reference.

The at least one primary tackifier used in the present invention will have a solubility parameter corresponding to δ and the block copolymer will have at least one segment whose solubility parameter corresponds to δ±2, preferably δ±1.7, more preferably δ±1.5, more preferably δ±1.3, more preferably δ±1.0, more preferably δ±0.7, more preferably δ±0.5, and more preferably δ±0.3.

In some embodiments, the primary tackifier may have a softening point (Ring and Ball, as measured by ASTM E-28) of 80° C. to 150° C., preferably 100° C. to 130° C. In other embodiments the primary tackifier may be liquid and have an R and B softening point of between about −70° C. and 70° C.

In some embodiments, the primary tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the trade name Regalite®. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may also be employed without departing from the spirit of the invention.

A particularly preferred primary tackifier for use in the present invention is a hydrogenated hydrocarbon resin derived from styrene, methyl styrene, and indene monomers, commercially available from Eastman under the tradename Regalite® R1100 (also known as hydrogenated styrene/methyl styrene/indene copolymer).

The at least one primary tackifier is present in the composition of the invention in an amount ranging from about 1% to about 50% by weight, preferably from about 5% to about 40% by weight, or more preferably from about 10% to about 30% by weight, relative to the total weight of the composition.

Secondary Tackifier

It may, at times, be desirable to also employ at least one secondary tackifier in the composition of the present invention. The at least one secondary tackifier is chosen from a hydrogenated polycyclopentadiene, commercially available from Kobo under the tradename Koboguard® 5400 IDD.

The at least one secondary tackifier, if employed, will be present in an amount of from about 0.5% to about 20% by weight, preferably from about 1% to about 15% by weight, or more preferably from about 2% to about 10% by weight, relative to the total weight of the composition.

High Viscosity Ester

The cosmetic composition of the present invention also contains at least one high viscosity ester. Examples thereof include, but not limited to, $C_1$-$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Suitable liquid esters include, but are not limited to: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Suitable solid esters may include, but are not limited to: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. In an embodiment, the ester is a sucrose polyester in which the degree of esterification is 7-8, and in which the fatty acid moieties are $C_{18}$ mono- and/or di-unsaturated and behenic, in a molar ratio of unsaturates:behenic of 1:7 to 3:5. In another embodiment, the sugar polyester is the octaester of sucrose in which there are about 7 behenic fatty acid moieties and about oleic acid moiety in the molecule. Other materials may include cottonseed oil or soybean oil fatty acid esters of sucrose.

A preferred high viscosity ester for use in the present invention is sucrose acetate isobutyrate. One example of a suitable sucrose acetate isobutyrate compound is SAIB-100®, commercially available from Eastman®, Kingsport, Tenn. It has a viscosity of about 100,000 cps at 30° C. and a refractive index of about 1.5 at 20° C.

The at least one high viscosity ester is present in the composition of the invention in an amount of from about 1% to about 50% by weight, preferably from about 1.5% to about 30% by weight, or more preferably from about 2% to about 10% by weight, relative to the total weight of the composition.

Alkoxylated Mixed Polyesters

According to the present invention, compositions comprising at least one alkoxylated mixed polyester are provided. As used herein, the term "mixed ester" means an ester obtained by reacting a polycarboxylic acid with at least two different alcohols.

According to preferred embodiments, the alkoxylated ester may be chosen from mixed esters of an alkoxylated alcohol and of a monohydric alcohol with polycarboxylic acids, such as dicarboxylic acids. For example, the alkoxylated ester may be chosen from mixed esters of a polyalkoxylated fatty alcohol and of a monohydric fatty alcohol with dicarboxylic fatty acids.

As used herein, the term "fatty acid" means an aliphatic carboxylic acid containing at least three carbon atoms. Non-limiting examples of fatty acids that are suitable for use in the present disclosure include those containing carbon, hydrogen and oxygen atoms. These fatty acids may be saturated and/or may comprise at least one carbon-carbon double bond. According to preferred embodiments, the fatty acid may be chosen from carboxylic acids obtained by the hydrolysis of fats or of plant or animal oils.

Examples of the mixed ester include, but are not limited to, compounds having the following structural formula:

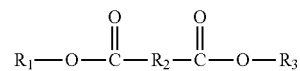

in which $R_1$ has the structural formula:

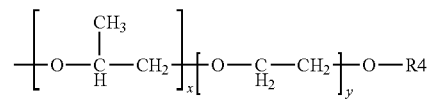

in which $R_4$ is a saturated or unsaturated, substituted or unsubstituted aliphatic unit containing from 4 to 24 carbon atoms;

x is an integer from 3 to 30;

y is an integer from 3 to 30;

$R_2$ is a saturated or unsaturated, substituted or unsubstituted aliphatic unit containing from 4 to 40 carbon atoms; and $R_3$ is a saturated or unsaturated, straight-chain or branched-chain aliphatic unit containing from 4 to 32 carbon atoms, for example, from 12 to 24 carbon atoms.

Non-limiting examples of compounds corresponding to the above general formula include octyldodecyl/PPG-3 myristyl ether dimer dilinoleate, sold under the reference Liquiwax™ polyEFA by the company Arch Chemical; stearyl PPG-3 myristyl ether dilinoleate, sold under the reference Liquiwax™ polyIPL by the company Arch Chemical; and isostearyl PPG-4 butyloctyl ether dilinoleate.

Mixed esters may be produced by reacting alkoxylated fatty alcohols and monohydric fatty alcohols with dicarboxylic fatty acids. According to preferred embodiments, the alkoxylated fatty alcohols may be chosen from propoxylated fatty alcohols having a carbon chain length ranging from 4 to 24 carbon atoms and a degree of propoxylation ranging from 3 to 30, for example, from 3 to 15 propylene oxide units.

Non-limiting examples of propoxylated fatty alcohols include myristyl alcohol and butyloctanol.

Non-limiting examples of dicarboxylic acids that are suitable for use in the present disclosure include malonic acid, succinic acid, glutaric acid, adipic acid, pimelic acid, suberic acid, azelaic acid, sebacic acid, 1,9-nonamethylenedicarboxylic acid, 1,10-decamethylenedicarboxylic acid, 1,11-undecamethylenedicarboxylic acid, 1,12-dodecamethylenedicarboxylic acid, 1,13-tridecamethylenedicarboxylic acid, 1,14-tetradeca-methylenedicarboxylic acid, 1,15-pentadecamethylenedicarboxylic acid, 1,16-hexadecamethylenedicarboxylic acid, and mixtures thereof. Further, the dicarboxylic acid may also be a diacid dimer. As used herein, the term "diacid dimer" denotes a diacid obtained via an intermolecular polymerization, for example, dimerization, reaction of at least one unsaturated monocarboxylic acid. For example, these diacid dimers may be derived from the dimerization of an unsaturated fatty acid, such as an unsaturated C8-34 fatty acid, for example, a C12-22 fatty acid, such as a C16-20 fatty acid, for example a C18 fatty acid. Examples of these unsaturated fatty acids include, but are not limited to undecenoic acid, linderic acid, myristoleic acid, palmitoleic acid, oleic acid, linoleic acid, elaidinic acid, gadolenoic acid, eicosapentaenoic acid, docosahexaenoic acid, erucic acid, brassidic acid, arachidonic acid, and mixtures thereof.

Further non-limiting examples of the mixed esters of the present invention and their preparation are provided in International Patent Application Publication No. WO 2004/052 076 and U.S. patent application publication no. 2006/0171910, the content of both of which are herein incorporated by reference in their entirety.

A particularly preferred alkoxylated mixed polyester for use in the present invention is octyldodecyl/PPG-3 myristyl ether dimer dilinoleate, sold under the reference Liquiwax™ polyEFA by Arch Personal Care Products L.P.

According to preferred embodiments, the at least one alkoxylated mixed polyester is present in the composition in an amount ranging from about 1% to about 50% by weight, preferably from about 2% to about 30% by weight, or more preferably from about 3% to about 10% by weight, relative to the total weight of the composition.

Waxes

The cosmetic compositions in accordance with the present invention also contain at least one wax. Suitable waxes are those generally used in cosmetics and dermatology. Examples thereof include, but are not limited to, those of natural origin such as beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil. Examples of suitable synthetic waxes include, but are not limited to, polyethylene waxes derived from the polymerization of ethylene, synthetic waxes, waxes obtained by Fischer-Tropsch synthesis, fatty acid esters and glycerides that are solid at 40° C., for example, at above 55° C., silicone waxes such as alkyl- and alkoxy-poly(di)methylsiloxanes and/or poly(di)methyl-siloxane esters that are solid at 40° C., for example, at above 55° C.

The at least one wax is present in the composition of the present invention in an amount of from greater than 0% to about 30%, based on the weight of the composition.

Solvent

The cosmetic composition of the present invention comprises at least one solvent. The at least one solvent may be chosen from a volatile silicone oil, a volatile hydrocarbon oil, a non-volatile silicone oil, a non-volatile hydrocarbon oil, esters other than those described above, and mixtures thereof.

Suitable volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Examples of volatile silicone oils that may be used include, but are not limited to, octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane, and their mixtures. Preferably, the volatile silicone oils have a flash point of at least 40° C.

Suitable volatile hydrocarbon oils include, but are not limited to, those having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile hydrocarbon oils have a flash point of at least 40° C.

Suitable non-volatile silicone oils that may be used include, but are not limited to, linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes, 2-phenylethyl trimethylsiloxysilicates, trimethyl pentaphenyl trisiloxane, tetramethyl hexaphenyl trisiloxane.

Suitable non-volatile hydrocarbon oils which can be used in the compositions of the present invention include, but are not limited to, polar oils such as:

oils with a high triglyceride content consisting of fatty acid esters of glycerol, the fatty acids of which may have varied chain lengths, these chains possibly being linear or branched, and saturated or unsaturated, such as tricaprylin; or these oils may be hydrocarbon-based plant oils such as wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R^2COOR^3$ in which $R^2$ represents a linear or branched higher fatty acid residue containing from 1 to 40 carbon atoms, including from 7 to 19 carbon atoms, and $R^3$ represents a branched hydrocarbon-based chain containing from 1 to 40 carbon atoms, including from 3 to 20 carbon atoms, with $R^2+R^3 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters; or esters of formula $R^4COOR^5COOR^6$ in which $R^4$ and $R^6$ each represent a linear or branched higher fatty acid residue containing from 1 to 40 carbon atoms, including from 7 to 19 carbon atoms, and $R^5$ represents a branched hydrocarbon-based chain containing from 1 to 40 carbon atoms such as for example neopentyl glycol dicaprate; or esters of formula $R^8COOR^9$ in which $R^8$ or $R^9$ each represent a linear or branched higher fatty acid residue containing from 1 to 40 carbon atoms;

synthetic ethers containing from 10 to 40 carbon atoms;

$C_8$ to $C_{26}$ fatty alcohols, for instance oleyl alcohol; and mixtures thereof.

The at least one solvent is present in the composition of the present invention in an amount of from greater than 0% to about 80% by weight, such as about 10% to about 80% by weight, such as about 20% to about 70% by weight, such as about 30% to about 60% by weight, based on the weight of the composition.

Colorant

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation.

Gelling Agents

The compositions of the invention may also be optionally gelled with an oil-phase gelling agent. The gelling agent increases the viscosity of the composition and leads to a solid or flowable composition. The gelling agent does not encompass waxes, in the sense that it is not waxy. The at least one gelling agent may be chosen from gelling agents in polymeric form and gelling agents in mineral form. The gelling agent may be chosen from agents that gel via chemical cross-linking and agents that gel via physical cross-linking.

Modified clays may be used as gelling agents, examples of which include, but are not limited to, hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34® by the company Rheox, Claytone XL®, Claytone 34® and Claytone 40® sold or made by the company Southern Clay, the modified clays known under the name quaternium-18 benzalkonium bentonites and sold or made under the names Claytone HT®, Claytone GR® and Claytone PS® by the company Southern Clay, the clays modified with stearyldimethylbenzoylammonium chloride, known as stearalkonium bentonites, such as the products sold or made under the names Claytone APA® and Claytone AF® by the company Southern Clay, and Baragel 24® sold or made by the company Rheox.

Other mineral gelling agents, which can be used in the invention, include silica, such as fumed silica. The fumed silica may have a particle size, which may be nanometric to micrometric, for example ranging from 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be: trimethylsiloxyl groups, which are obtained in particular by treating fumed silica in the presence of hexamethyldisilazane. Silicas thus treated are known as "silica silylate" according to the CTFA dictionary (6th edition, 1995). They are sold or made, for example, under the references "Aerosil R812®" by the company Degussa and "CAB-O-SIL TS-530®" by the company Cabot; dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA dictionary (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot; groups derived from reacting fumed silica with silane alkoxides or siloxanes. These treated silicas are, for example, the products sold or made under the reference "Aerosil R805®" by the company Degussa.

According to the invention, hydrophobic silica, such as fumed silica, may be used as a lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one lipophilic gelling agent can allow the exudation of the composition to be limited and can allow its stability to be increased, while at the same time conserving the composition's glossy appearance, which is not possible with waxes such as those used conventionally in cosmetics and dermatology.

The at least one gelling agent, if used, will typically be present in the composition of the present invention in an amount of from greater than 0% to 20% by weight, based on the weight of the composition.

Volatile Solvents

There may be instances where the use of a polar volatile solvent is desired. Such solvents may include, but are not limited to, alcohols, volatile esters and volatile ethers. In general, they will have a flash point below about 25° C.

Additives/Auxiliary Agents

The compositions of the present invention may further comprise at least one cosmetically or dermatologically acceptable additive such as a thickener, a film former, a plasticizer, an antioxidant, an essential oil, a preserving agent, a fragrance, a filler, a pasty fatty substance, a waxy fatty substance, a neutralizing agent, and a polymer, and cosmetically active agents and/or dermatological active agents such as, for example, emollients, moisturizers, vitamins, essential fatty acids and medicaments.

While the use of a plasticizer is not necessary in the compositions of the present invention, it may, nevertheless, be desirable. Plasticizers are organic compounds added to a high polymer both to facilitate processing and to increase the flexibility and toughness of the final product by internal modification of the polymer molecule. Examples of suitable plasticizers include, but are not limited to, oils, cellulose esters, phthalate esters, adipate esters, sebacate esters, tricresyl phosphate, castor oil, glycol ethers, benzyl alcohol, triethyl citrate, and propylene carbonate.

Representative examples of preservatives include alkyl para-hydroxybenzoates, wherein the alkyl radical has from 1, 2, 3, 4, 5 or 6 carbon atoms and preferably from 1 to carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Mixtures of preservatives may certainly be used, e.g., the mixture of methyl-paraben, ethylparaben, propylparaben and butylparaben sold under the name Nipastat by Nipa, and the mixture of phenoxyethanol, methylparaben, ethylparaben, propylparaben and butylparaben sold under the name Phenonip, also by Nipa. These preservatives may be present in amounts ranging from about 0.01 to about 10% by weight, preferably from 0.5% to about 5% by weight, and more preferably from about 0.8 to about 3% by weight, based on the weight of the composition.

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel® by the company Kemanord Plast or under the name Micropearl F® 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo® by the company National Starch; silicone resin microbeads such as those sold under the name Tospearl® by the company Toshiba Silicone; clays (bentone, laponite, saponite, etc.) and mixtures thereof. These fillers may be present in amounts ranging from greater than 0% to 50% by weight, based on the weight of the composition.

The compositions of the present invention may further comprise a safe and effective amount of at least one active ingredient or pharmaceutically acceptable salt thereof. The term "safe and effective amount" as used herein, means an amount sufficient to modify the condition to be treated or to deliver the desired skin benefit, while at the same time avoiding serious side effects, at a reasonable benefit to risk ratio within the scope of sound medical judgment. What is a safe and effective amount of the active ingredient will vary with the specific active agent, the ability of the active agent to penetrate through the skin, the age, health and skin condition of the user, and other like factors. Typically, the active ingredient may be present in amounts ranging from greater than 0% to 20% by weight, based on the weight of the composition.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically acceptable salts of these active ingredients are useful herein. The following active ingredients are useful in the compositions of the present invention.

The cosmetic compositions of the present invention may also contain sunscreens, which are chemical absorbers that actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol® 1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

Examples of suitable sunscreens include, but are not limited to: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N, N, N-trimethyl-4-(2-oxoborn-3-ylidene methyl)anillinium methyl sulfate, and mixtures thereof.

It has been surprisingly discovered that the composition of the present invention delivers liquid-like shine effect, that is, high shine, and long lasting shine properties, as well as good wear, a non-tacky feel, comfort, cushion, moisturization and desirable creamy texture characteristics upon application onto skin.

It has also been surprisingly discovered that the association of a block copolymer, at least one primary tackifier, a high viscosity ester and an alkoxylated mixed polyester in the presence of at least one solvent and at least one wax results in the formation of an anhydrous composition having high shine and longer lasting shine properties on skin, such as the lips and the face, while providing good wear, superior comfort, a non-tacky feel and cushioning to the skin. At the same time, when the composition of the present invention is in the form of a lipstick, it was found that the lipstick exhibited minimum feathering and migration properties.

The composition of the present invention may be in the form of a liquid, semi solid such as a gel, or a solid. The cosmetic compositions may be used to make up the lips such as lip glosses or lipsticks or to make up eyelids such as eyeshadows. The compositions may also be used as hair cosmetic compositions.

The composition of the present invention may be anhydrous or non anhydrous, in the form of an aqueous emulsion, such as oil in water (O/W), water in oil (W/O), or a multiple emulsion (W/O/W, O/WO, . . . ), or non aqueous emulsion, in which case the water is replaced with a material compatible with water, such as a diol, alcohol, glycol, polyhydric alcohol and derivatives thereof. By anhydrous, it is meant that the composition contains no added water (other than the water that may be provided by other components of the composition such as a latex or the like).

The present invention is further described in terms of the following non-limiting examples. Unless otherwise indicated, all parts and percentages are on a weight-by-weight percentage basis.

EXAMPLE

Examples

Lipstick Formulations

| Ingredient names | A % | B % |
|---|---|---|
| HYDROGENATED STYRENE/BUTADIENE COPOLYMER (Kraton G1657M ®) | 3.7 | 3 |
| HYDROGENATED STYRENE/METHYL STYRENE/INDENE COPOLYMER (Regalite ® R1100) | 11 | 12 |
| HYDROGENATED POLYCYCLOPENTADIENE (Koboguard ® 5400 IDD) | | 7 |
| HYDROGENATED POLYDECENE | 18.3 | 15 |
| POLYETHYLENE* | 5.5 | 5.5 |
| POLYETHYLENE** | 3.5 | 4 |

-continued

| Ingredient names | A % | B % |
|---|---|---|
| SUCROSE ACETATE ISOBUTYRATE | 3 | 3 |
| TRIMETHYL PENTAPHENYL TRISILOXANE | 10 | 10 |
| BEESWAX | 2 | 1.5 |
| OCTYLDODECYL/PPG-3 MYRISTYL ETHER DIMER DILINOLEATE | 5 | 5 |
| NEOPENTYL GLYCOL DICAPRATE AND STEARYL HEPTANOATE | 21 | 19 |
| BLUE 1 LAKE | | 0.2 |
| RED 7 | 0.45 | 0.45 |
| YELLOW 5 LAKE | 0.13 | |
| MICA, TITANIUM DIOXIDE | 5.5 | 5.6 |
| IRON OXIDES | 0.95 | 0.95 |
| BOROSILICATES | | |
| ALUMINA | 0.9 | |
| TRICAPRYLIN | QS | QS |

*Permaformalene ® 400 from the supplier New Phase Techonolgies
**Permaformalene ® 500-L from the supplier New Phase Techonolgies Method of Making:

Procedure for Phase A:

Hydrogenated polydecene, cctyldodecyl/PPG-3 myristyl ether dimer dilinoleate, sucrose aetate isobutyrate, trimethyl pentaphenyl trisiloxane, and hydrogentate styrene/butadiene copolymer were mixed, and the mixture was heated to 100° C. while mixing. Hydrogenated styrene/methyl styrene/indene copolymer was slowly added and mixing was continued until homogeneous on lowest speed.

Procedure for Pigment Grind:

The pigments were combined with a portion of Phase A and ground in a discontimill.

The other waxes, pigment grind, and other ingredients were combined with Phase A and mixed at 99° C. until the resulting mixture was homogeneous. The mixture was slightly cooled and poured to form the sticks.

The formulations above exhibited the properties of good wear, minimal migration, and high shine when applied on lips and which lasted for at least 2 hours.

It is to be understood that the foregoing describes preferred embodiments of the invention and that modifications may be made therein without departing from the spirit or scope of the invention as set forth in the claims.

What is claimed is:

1. A method of making up keratinous substrates involving applying onto the keratinous substrates a composition comprising:
(a) at least one block copolymer chosen from at least one di-block copolymer comprised of a styrene monomer in combination with at least one other monomer chosen from ethylene and butylene, at least one tri-block copolymer comprised of at least two styrene monomers in combination with at least one other monomer chosen from ethylene and butylene, and a mixture of the at least one di-block copolymer and the at least one tri-block copolymer;
(b) at least one primary tackifier chosen from hydrogenated styrene/methyl styrene/indene copolymers;
(c) at least one high viscosity ester comprising sucrose acetate isobutyrate;
(d) at least one alkoxylated mixed polyester chosen from octyldodecyl/PPG-3 myristyl ether dimer dilinoleate, stearyl PPG-3 myristyl ether dilinoleate and isostearyl PPG-4 butyloctyl ether dilinoleate, wherein the at least one alkoxylated mixed polyester is present in an amount of about 3% to about 10% by weight, based on the weight of the composition;

(e) at least one wax;
(f) at least one solvent; and
(g) optionally, a colorant.

2. The method according to claim 1 wherein (a) is comprised of about 29% by weight of the at least one di-block copolymer and about 71% by weight of the at least one tri-block copolymer, all weights based on the total weight of the block copolymer.

3. The method according to claim 1, wherein (a) is present in an amount of from about 0.1% to about 30% by weight, based on the weight of the composition.

4. The method according to claim 1, wherein (b) is present in an amount of from about 1% to about 50% by weight, based on the weight of the composition.

5. The method according to claim 1, wherein (c) is present in an amount of from about 1% to about 50% by weight, based on the weight of the composition.

6. The method according to claim 1, wherein (c) has a viscosity of about 100,000 cps at 30° C. and a refractive index of about 1.5 at 20° C.

7. The method according to claim 1, wherein (d) is octyldodecyl/PPG-3 myristyl ether dimer dilinoleate.

8. (withdrawn - currently amended) The method according to claim 1, wherein (d) is present in an amount of about 5% by weight, based on the weight of the composition.

9. The method according to claim 1, wherein (e) is present in an amount of from greater than 0% to about 30% by weight, based on the weight of the composition.

10. The method according to claim 1, wherein (f) is present in an amount of from about 10% to about 80% by weight, based on the weight of the composition.

11. The method according to claim 1, wherein (g) is present in an amount effective to impart color when applied onto keratinous substrates.

12. The method according to claim 1, wherein the composition further comprises at least one secondary tackifier.

13. The method according to claim 12, wherein the at least one secondary tackifier is a hydrogenated polycyclopentadiene.

14. The method according to claim 12, wherein the at least one secondary tackifier is present in an amount of from about 0.5% to about 20% by weight, based on the weight of the composition.

15. The method according to claim 1, wherein the composition is a lipstick.

16. A cosmetic composition comprising:
(a) at least one block copolymer chosen from at least one di-block copolymer comprised of a styrene monomer in combination with at least one other monomer chosen from ethylene and butylene, at least one tri-block copolymer comprised of at least two styrene monomers in combination with at least one other monomer chosen from ethylene and butylene, and a mixture of the at least one di-block copolymer and the at least one tri-block copolymer;
(b) at least one primary tackifier chosen from hydrogenated styrene/methyl styrene/indene copolymers;
(c) at least one high viscosity ester comprising sucrose acetate isobutyrate;
(d) at least one alkoxylated mixed polyester chosen from octyldodecyl/PPG-3 myristyl ether dimer dilinoleate, stearyl PPG-3 myristyl ether dilinoleate and isostearyl PPG-4 butyloctyl ether dilinoleate, wherein the at least one alkoxylated mixed polyester is present in an amount of about 3% to about 10% by weight, based on the weight of the composition;
(e) at least one wax;
(f) at least one solvent; and
(g) optionally, a colorant.

17. The composition according to claim 16 wherein (a) is comprised of about 29% by weight of the at least one di-block copolymer and about 71% by weight of the at least one tri-block copolymer, all weights based on the total weight of the block copolymer.

18. The composition according to claim 16, wherein (a) is present in an amount of from about 0.1% to about 30% by weight, based on the weight of the composition.

19. The composition according to claim 16, wherein (b) is present in an amount of from about 1% to about 50% by weight, based on the weight of the composition.

20. The composition according to claim 16, wherein (c) is present in an amount of from about 1% to about 50% by weight, based on the weight of the composition.

21. The composition according to claim 16, wherein (c) has a viscosity of about 100,000 cps at 30° C. and a refractive index of about 1.5 at 20° C.

22. The composition according to claim 16, wherein (d) is octyldodecyl/PPG-3 myristyl ether dimer dilinoleate.

23. The composition according to claim 16, wherein (d) is present in an amount of about 5% by weight, based on the weight of the composition.

24. The composition according to claim 16, wherein (e) is present in an amount of from greater than 0% to about 30% by weight, based on the weight of the composition.

25. The composition according to claim 16, wherein (f) is present in an amount of from about 10% to about 80% by weight, based on the weight of the composition.

26. The composition according to claim 16, wherein (g) is present in an amount effective to impart color when applied onto keratinous substrates.

27. The composition according to claim 16, wherein the composition further comprises at least one secondary tackifier.

28. The composition according to claim 27, wherein the at least one secondary tackifier is a hydrogenated polycyclopentadiene.

29. The composition according to claim 27, wherein the at least one secondary tackifier is present in an amount of from about 0.5% to about 20% by weight, based on the weight of the composition.

30. The composition according to claim 16, wherein the composition is a lipstick.

31. A cosmetic composition comprising:
(a) from about 1% to about 20% by weight of at least one block copolymer comprised of:
  (i) about 29% by weight of at least one di-block copolymer; and
  (ii) about 71% by weight of at least one tri-block copolymer,
  wherein the weights of (i) and (ii) are based on the total weight of the at least one block copolymer, and wherein the at least one di-block copolymer is comprised of a styrene monomer in combination with at least one other monomer chosen from ethylene and butylene and the at least one tri-block copolymer is comprised of at least two styrene monomers in combination with at least one other monomer chosen from ethylene and butylene;
(b) from about 10% to about 30% by weight of a hydrogenated styrene/methyl styrene/indene copolymer;
(c) from about 2% to about 10% by weight of sucrose acetate isobutyrate;
(d) from about 3% to about 10% by weight of octyldodecyl/PPG-3 myristyl ether dimer dilinoleate;

(e) from greater than 0% to about 30% by weight of at least one wax;

(f) from about 30% to about 60% by weight of at least one solvent; and (g) optionally, a colorant, wherein the weights of (a)-(f) are based on the total weight of the composition.

32. The composition according to claim 16, wherein (a) is comprised of (i) at least one di-block copolymer comprised of a styrene monomer in combination with at least one other monomer chosen from ethylene and butylene; and (ii) at least one triblock copolymer comprised of at least two styrene monomers in combination with at least one other monomer chosen from ethylene and butylene.

33. The composition according to claim 16, wherein (d) is chosen from stearyl PPG-3 myristyl ether dilinoleate and isostearyl PPG-4 butyloctyl ether dilinoleate.

34. The composition according to claim 16, wherein (e) is chosen from beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils, polyethylene waxes, waxes obtained by Fischer-Tropsch synthesis, fatty acid esters and glycerides that are solid at 40° C., fatty acid esters and glycerides that are solid at above 55° C., and silicone waxes.

35. The composition according to claim 31, wherein the composition further comprises at least one secondary tackifier comprising hydrogenated polycyclopentadiene and present in an amount of from about 2% to about 10% by weight, based on the weight of the composition.

36. The method according to claim 1, wherein (a) is comprised of (i) at least one di-block copolymer comprised of a styrene monomer in combination with at least one other monomer chosen from ethylene and butylenes; and (ii) at least one tri-block copolymer comprised of at least two styrene monomers in combination with at least one other monomer chosen from ethylene and butylene.

37. The method according to claim 1, wherein (d) is chosen from stearyl PPG-3 myristyl ether dilinoleate and isostearyl PPG-4 butyloctyl ether dilinoleate.

38. The method according to claim 1, wherein (e) is chosen from beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils, polyethylene waxes, waxes obtained by Fischer-Tropsch synthesis, fatty acid esters and glycerides that are solid at 40° C., fatty acid esters and glycerides that are solid at above 55° C., and silicone waxes.

39. The method according to claim 1, wherein the composition further comprises at least one secondary tackifier comprising hydrogenated polycyclopentadiene and present in an amount of from about 2% to about 10% by weight, based on the weight of the composition.

40. The composition of claim 16, wherein (a) is chosen from at least one di-block copolymer comprised of a styrene monomer in combination with at least one other monomer chosen from ethylene and butylene, at least one tri-block copolymer comprised of at least two styrene monomers in combination with at least one other monomer chosen from ethylene and butylene, and a mixture of the at least one di-block copolymer and the at least one tri-block copolymer; (b) is a hydrogenated styrene/methyl styrene/indene copolymers; wherein (c) is sucrose acetate isobutyrate; and wherein (d) is octyldodecyl/PPG-3 myristyl ether dimer dilinoleate.

* * * * *